(12) United States Patent
Faulks et al.

(10) Patent No.: US 6,315,764 B1
(45) Date of Patent: Nov. 13, 2001

(54) ABSORBENT ARTICLE HAVING A REAR RESERVOIR WITH VOID VOLUME CAPACITY

(75) Inventors: Michael John Faulks, Neenah; Paul John Serbiak, Appleton; Jody Dorothy Suprise, Neenah, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 408 days.

(21) Appl. No.: 08/575,926

(22) Filed: Dec. 20, 1995

(51) Int. Cl.$^7$ .................................................. A61F 13/15
(52) U.S. Cl. .............................. 604/385.24; 604/385.01
(58) Field of Search .............................. 604/385.1, 385.2, 604/378, 383

(56) References Cited

U.S. PATENT DOCUMENTS

| | | | |
|---|---|---|---|
| Re. 33,106 | 11/1989 | Beckestrom | 604/385.2 |
| 3,978,861 | 9/1976 | Schaar | 128/287 |
| 4,500,316 | 2/1985 | Damico | 604/389 |
| 4,701,173 * | 10/1987 | Zehner et al. | 604/385.2 |
| 4,704,115 | 11/1987 | Buell | 604/385 |
| 4,718,900 | 1/1988 | Boland et al. | 604/385 |
| 4,753,646 | 6/1988 | Enloe | 604/385 |
| 4,808,176 * | 2/1989 | Kielpikowski | 604/385.2 |
| 4,808,177 | 2/1989 | DesMarais et al. | 604/385.1 |
| 4,846,825 | 7/1989 | Enloe et al. | 604/385.1 |
| 4,850,990 | 7/1989 | Huntoon et al. | 604/385.2 |
| 4,861,652 * | 8/1989 | Lippert et al. | 604/385.1 |
| 4,938,755 | 7/1990 | Foreman | 604/385.2 |
| 4,988,344 | 1/1991 | Reising et al. | 604/368 |
| 4,988,345 | 1/1991 | Reising | 604/368 |
| 5,069,672 | 12/1991 | Wippler et al. | 604/385.1 |
| 5,137,526 | 8/1992 | Coates | 604/391 |
| 5,171,236 | 12/1992 | Dreier et al. | 604/369 |
| 5,176,672 | 1/1993 | Bruemmer et al. | 604/385.1 |
| 5,187,817 | 2/1993 | Zolner | 2/400 |
| 5,207,662 | 5/1993 | James | 604/385.2 |
| 5,221,274 * | 6/1993 | Buell et al. | 604/385.1 |
| 5,234,423 | 8/1993 | Alemany et al. | 604/385.2 |
| 5,246,431 | 9/1993 | Minetola et al. | 604/385.2 |
| 5,370,634 * | 12/1994 | Ando et al. | 604/385.1 |
| 5,489,282 * | 2/1996 | Zehner et al. | 604/385.1 |
| 5,514,121 * | 5/1996 | Roe et al. | 604/385.1 |

FOREIGN PATENT DOCUMENTS

| | | |
|---|---|---|
| 486006A2 | 5/1992 | (EP) . |
| WO9428844 | 12/1994 | (WO) . |
| WO9607381 | 3/1996 | (WO) . |

\* cited by examiner

Primary Examiner—Dennis Ruhl
(74) Attorney, Agent, or Firm—Wilhelm Law Service; Thomas D. Wilhelm; Alyssa A. Dudkowski (57) ABSTRACT

An absorbent article includes a rear reservoir to receive and hold fecal and other body exudates. The rear reservoir preferably includes a spacer located at a rear portion preferably between a bodyside liner layer and an outer cover layer, assisting in formation of the rear reservoir. A rear waist flap, preferably comprised of the base structure of the absorbent article can be folded inwardly from the rear edge to form, in combination with the spacer and optionally other elements of the absorbent article, the rear reservoir. The rear waist flap can alternatively be formed by a separate element attached to the rear portion of the absorbent article. The separate element can comprise an elastic member, or a nonelastic member with rear waist elastics. The rear waist flap preferably is substantially stretched with respect to the rear portion to assist in shaping the rear reservoir. The spacer preferably comprises an internal filler, and has a rod-like shape.

45 Claims, 5 Drawing Sheets

ABSORBENT ARTICLE HAVING A REAR RESERVOIR WITH VOID VOLUME CAPACITY

FIELD OF THE INVENTION

Absorbent articles such as infant diapers, training pants, adult incontinence products, and the like are well known. Such articles have achieved a wide acceptance due to their ability to receive and absorb body exudates.

This invention pertains to an absorbent article for containing body exudates. Such absorbent articles generally utilize leg cuffs to help prevent leakage of body exudates. This invention utilizes a rear reservoir to prevent leakage of exudates, and especially fecal material.

BACKGROUND OF THE INVENTION

In general, body exudates of urine and fecal material should be received and contained by the absorbent article. However, leakage problems are common, especially leakage of exudate material which has not been absorbed by the absorbent material in the absorbent article. In general urine will be substantially all absorbed. Fecal material, by contrast, is absorbed only in part, and even the partial absorption tends to occur more slowly. This invention is directed generally toward the exudate material which has never been absorbed, as opposed to exudate material which has been absorbed into the absorbent core or other absorbent element.

Leakage generally occurs for one of two reasons. First, the exudates may be released from the user's body so rapidly that the absorption rate of the absorbent article is temporarily overpowered. In such case, the excess exudates need only be held and contained at the surface of the absorbent article for a short period of e.g. a few seconds until absorption into the absorbent article catches up with release from the body, and all readily absorbable exudate material becomes absorbed.

Second, the exudate material, especially fecal material, which is absorbed by the absorbent core more slowly than urine, may move laterally along the body-side surface of the absorbent article, to an edge of the interfacial area defined between the absorbent article and the user's body. To the extent there is an effective seal between the absorbent article and the user's body at the respective edge portion, the exudate material is retained and held between the absorbent article and the user's body pending absorption of readily absorbable portions of the exudate material. However, should there be no seal, or if the seal is ineffective or otherwise insufficient, the exudate material can move past the edge and out from between the absorbent article and the user's body. Such movement past the edge constitutes a failure of the absorbent article to perform its primary function, namely to contain the exudates.

Seal requirements for absorbent articles generally fall into three classes, namely side seals around the user's legs, front seals at the front of the user's trunk and rear seals at the rear of the user's trunk. Leg cuffs and leg flaps have been designed and implemented to prevent leakage in the sides, or leg regions, of diapers and the like. The need for front seals is somewhat limited in that the primary direction of exudate flow from the user's body is downwardly and to the rear.

The need for rear seals is significant. The problem of rear leakage is well known, especially in association with liquidous and/or explosive bowel movements, which are common in young children.

It is known to fold inwardly a flap at the rear of the absorbent article to prevent wicking of absorbed liquids to the rear edge of the absorbent article. With the in-folded rear flap, the outer cover layer generally provides a liquid barrier between the absorbent core, or the absorbent material, and the rear outer edge of the absorbent article.

The in-folded flap prevents leakage from absorbent material (in the absorbent article) to the outer edge of the absorbent article. However, it does not prevent leakage across the top surface of the in-folded flap, between the top surface of the infolded flap and the user's body.

It is also known to provide elastic properties, such as an elastic waist band, across the absorbent article at or adjacent the rear outer edge of the absorbent article. However, waist band and like elastics are not entirely effective to prevent movement of the exudate material out from between the absorbent article and the user's body. Indeed no structure has been devised in known art effective to prevent leakage of fecal material past the rear edge of diapers and like absorbent articles.

It is an object of this invention to provide an absorbent article which is effective to prevent leakage of fecal material past the rear edge of the absorbent article.

It is another object to provide an absorbent article having a rear containment reservoir for receiving and holding exudate material which has not been absorbed by the absorbent article.

It is still another object to provide a rear waist flap for disposition against the user's body, which provides an effective barrier to leakage of liquidous fecal and other material.

It is yet another object to provide elastic implementations which urge the distal edge of the rear waist flap away from the bodyside liner layer of the absorbent article and thus create an opening through which exudate material enters the rear containment reservoir.

It is a still further object to provide a spacer in the rear containment reservoir, holding open, for receiving exudates, a minimum volume of space in the rear containment reservoir.

SUMMARY OF THE INVENTION

This invention relates to an absorbent article designed to absorb and contain body exudates. This invention comprises an absorbent article having a rear reservoir which includes a rear waist flap to contain body exudates such as fecal material. A spacer is mounted to the rear portion of the absorbent article. The rear waist flap in combination with at least one of the spacer, the leg elastics, and the rear waist elastics form the rear reservoir.

In one aspect, the present invention resides in an absorbent article having a rear portion with a rear edge, a front portion, and a crotch portion connecting the rear portion and the front portion. The absorbent article comprises an outer cover layer; a bodyside liner layer mounted to the outer cover layer; a spacer mounted to the rear portion of the absorbent article, and extending across the absorbent article; and a rear reservoir defined in part by the spacer, adjacent the rear edge, whereby the rear reservoir provides void volume capacity for a user of the absorbent article, the void volume capacity preventing leakage of exudates. A rear waist flap preferably extends from the rear edge outwardly around the spacer and toward the crotch portion of the absorbent article.

In some embodiments, the spacer can be located between the outer cover layer and the bodyside liner layer. The spacer can comprise a regenerated cellulose fluff blended with polyester. The spacer can also comprise a rod-like shaped structure which, in combination with rear waist flap, forms the rear reservoir.

The spacer preferably has first and second ends, and a midpoint, the spacer being bowed such that the midpoint of the spacer is displaced rearwardly of the absorbent article with respect to the first and second ends.

In some embodiments, the rear waist flap comprises portions of both the outer cover layer and the bodyside liner layer folded inwardly toward the bodyside liner layer of the rear portion, with the rear waist flap attached at opposing side edges thereof to the rear portion to thereby form the rear reservoir between the rear waist flap and the rear portion.

In another embodiment, the rear waist flap comprises an elastic member attached to the rear portion at the rear edge and opposing side edges. The elastic member can be substantially stretched when attached to the rear portion, the elastic member, when released from the stretched condition, retracting the rear portion to form in part the rear reservoir.

In yet another embodiment, the rear waist flap comprises a nonelastic material extending from the rear portion at the rear edge and opposing side edges, the nonelastic material having waist elastics attached thereto. Rear waist elastics are attached across the rear waist flap, the rear waist elastics, in combination with the spacer, the rear portion, and the rear waist flap, forming the rear reservoir by exerting a force shaping the rear reservoir. The rear reservoir has an opening for receiving exudates into the rear reservoir, the opening having a length extending across a width of the absorbent article generally corresponding to a respective width of the rear reservoir.

The rear waist flap, in combination with at least part of the rear portion of the absorbent article, extends in a "C" configuration.

In another aspect of the invention, first and second leg elastics are at respective opposing first and second side edges of the absorbent article in the crotch portion, the first and second leg elastics extending into the rear portion and assisting in forming an inwardly-opening pocket in the rear portion, forward of the rear edge. The inwardly-opening pocket is comprised in the rear reservoir.

The invention further comprehends an absorbent article having a rear portion with a rear edge, a front portion, a crotch portion connecting the rear portion and the front portion, the absorbent article comprising an outer cover layer; a bodyside liner layer mounted to the outer cover layer, and extending over the front portion, the rear portion, and the crotch portion; a rear waist flap mounted adjacent the rear edge of the rear portion and extending toward the crotch portion, the rear waist flap being spaced from the rear portion and forming a rear reservoir between the rear waist flap and the bodyside liner layer of the rear portion; and, an opening between the rear waist flap and the bodyside liner layer of the rear portion, for receiving exudates into the rear reservoir, the opening having a length extending across a width of the absorbent article corresponding to a respective width of the rear reservoir. The spacer generally extends across the absorbent article to space the rear waist flap from the rear portion.

The invention further comprehends an absorbent article having a front edge, a rear edge, and opposing first and second side edges, and including a rear portion having a distal edge thereof, a front portion, and a crotch portion connecting the rear portion and the front portion, the absorbent article comprising an outer cover layer; a bodyside liner layer mounted to the outer cover layer, the bodyside liner layer and the outer cover layer, in combination, comprising a base structure of the absorbent article; and a rear reservoir formed by a rear waist flap extending between the distal edge of the rear portion and the rear edge of the absorbent article, the rear waist flap being spaced from the rear portion, and facing the bodyside liner layer in the rear portion.

In another aspect, the invention includes a spacer mounted to at least one of the rear portion and the rear waist flap, the spacer and the rear edge extending across the absorbent article, the spacer, in combination with the rear portion and the rear waist flap, forming the rear reservoir. The rear reservoir also includes an opening for receiving exudates, the opening having a length extending across a width of the absorbent article generally corresponding to a respective width of the rear reservoir.

The rear waist flap can comprise portions of both the outer cover layer and the bodyside liner layer folded inwardly toward the bodyside liner layer of the rear portion, with the rear waist flap attached at opposing side edges thereof to the rear portion to thereby form the rear reservoir between the rear waist flap and the rear portion.

The invention is not limited in its application to the details of construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components.

DETAILED DESCRIPTION OF THE PREFERRED EMBODIMENTS

The present invention relates to absorbent articles designed to absorb body exudates. While the preferred embodiments of the present invention are described herein in terms of an absorbent article such as a diaper for an infant, the invention includes, and is equally applicable to, adult incontinent briefs, training pants and the like.

The present invention can best be understood by reference to the drawings where like numerals reference like elements.

Figure 1:
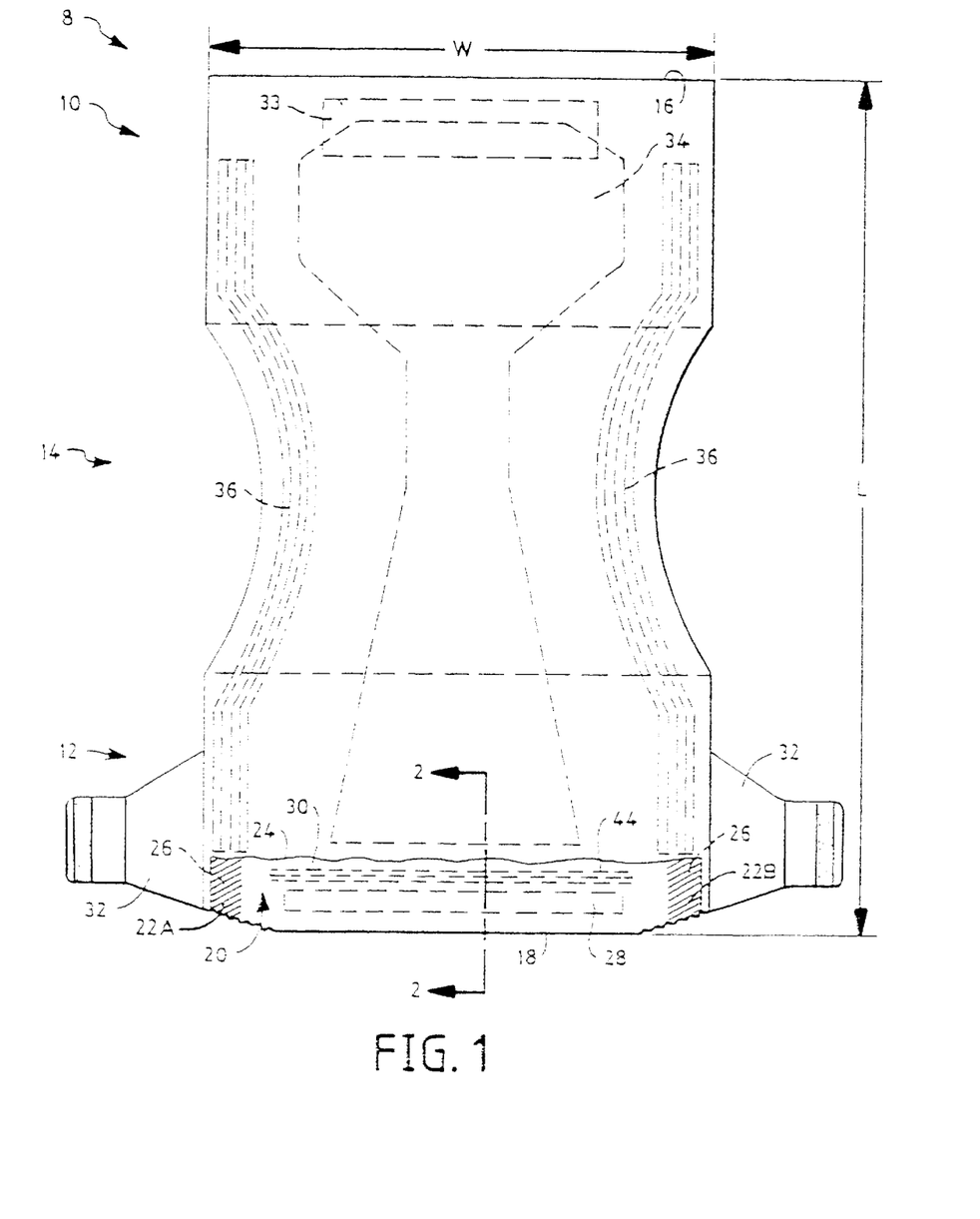
FIG. 1 illustrates a top view of a first embodiment of an absorbent article of the invention, fully extended.

FIG. 1 illustrates an absorbent article 8 with a front portion 10, a rear portion 12 and crotch portion 14 connecting the front portion 10 and the rear portion 12. The absorbent article 8 has a front edge 16 and a rear edge 18. The absorbent article 8 includes a rear waist flap 20 having side edges 22A, 22B and a distal edge 24. The rear waist flap 20 comprises a folded over length of the rear portion 12 in FIG. 1. Side edges 22A, 22B of the rear waist flap 20 are folded over and attached by glue 26 or other similar bonding techniques to the rear portion 12. A spacer 28 is mounted to the rear portion 12 adjacent the rear edge 18. The spacer 28, in combination with the rear waist flap 20, forms a rear reservoir 30. This rear reservoir 30 provides improved protection against leakage of exudates, and particularly fecal material because of its structure, and its location in the rear portion 12. The absorbent article 8 may also comprise a pair of attachment elements 32 in the rear portion 12 and an attachment surface 33 in the front portion 10 of the absorbent article 8 which in combination, attach the absorbent article 8 upon a user's body. An absorbent core 34 is mounted in the center of the absorbent article 8. The absorbent core 34 extends from the front portion 10, through the crotch portion 14, and into the rear portion 12. FIG. 1 also shows leg elastics 36 in the crotch portion 14 which gather the absorbent article 8 to provide an adjustable fit to a user. Leg elastics 36 extend across rear portion 12 generally to distal edge 24.

Figure 2:
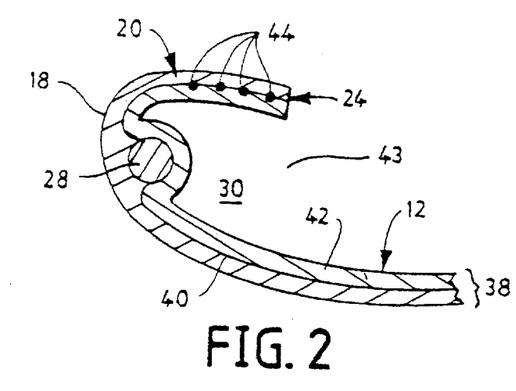
FIG. 2 illustrates a fragmentary cross-sectional view taken at 2—2 of FIG. 1.

FIG. 2 comprises a cross-sectional view of the rear portion 12 taken at 2—2 of FIG. 1. FIG. 2 shows a base structure 38 formed by an outer cover layer 40 and a bodyside liner layer 42. Spacer 28, attached to base structure 38, helps form reservoir 30. The rear waist flap 20 comprises a folded over length of the rear portion 12. Rear waist elastics 44 shown in FIGS. 1 and 2 also help form rear reservoir 30 by tensioning the rear waist flap 20.

Figure 7:
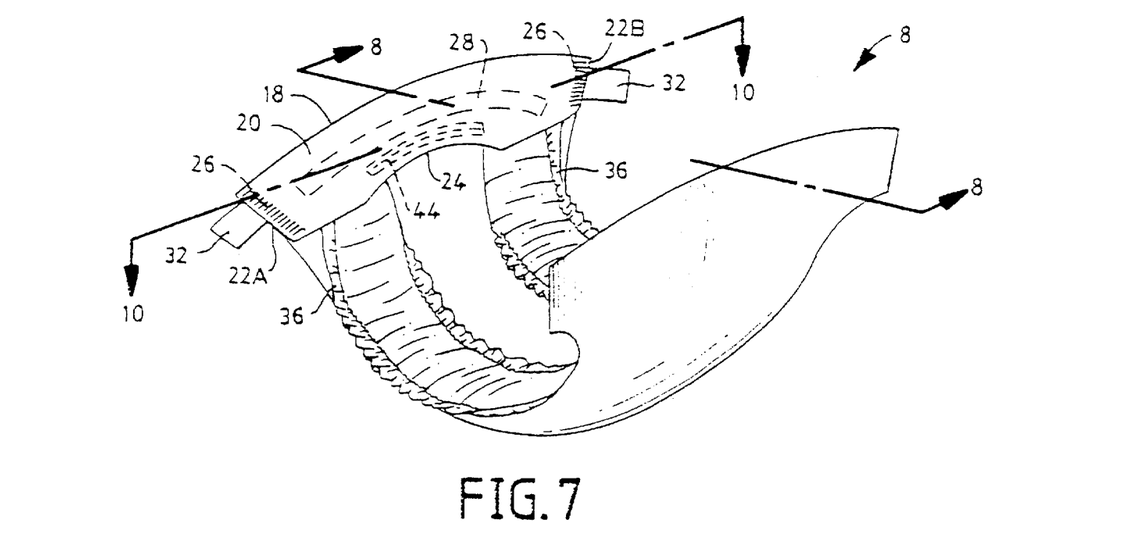
FIG. 7 illustrates a pictorial view of an absorbent article of the invention, showing generally its shape in use.

In a preferred embodiment, the ends of rear waist elastics 44 meet or overlap respective ends of leg elastics 36 such that tension on the leg elastics 36, which tends to form the relaxed absorbent article 8 into a cup shape as shown in FIG. 7, also tends to lift the distal edge 24 of rear waist flap 20 away from the bodyside liner layer 42 on rear portion 12, thus creating an opening 43 into rear reservoir 30. In the illustrated embodiments, the length of opening 43 extends across a width of absorbent article 8 generally corresponding to a respective width of the rear reservoir 30 between the side edges 22A, 22B.

The absorbent core 34 suitably comprises a matrix of hydrophilic fibers, such as a web of cellulosic fluff, preferably in combination with a high-absorbency material commonly known as superabsorbent material. In a preferred embodiment, absorbent core 34 comprises a mixture of superabsorbent hydrogel-forming material and wood pulp fluff. In place of the wood pulp fluff, one may use synthetic, polymeric, or meltblown fibers or a combination of meltblown fibers and natural fibers. The superabsorbent material may be substantially homogeneously mixed with the hydrophilic fibers or may be otherwise combined into the absorbent core.

Alternatively, the absorbent core 34 may comprise a laminate of fibrous webs and superabsorbent material or other suitable means of maintaining a superabsorbent material in a localized area.

The high-absorbency material in the absorbent core 34 can be selected from natural, synthetic and modified natural polymers and materials. The high absorbency materials can be inorganic materials, such as silica gels, or organic compounds, such as crosslinked polymers. The term crosslinked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

A suitable bodyside liner layer 42 may be manufactured from a wide selection of web materials, such as porous foams, reticulated foams, apertured plastic films or natural or synthetic fibers. For example, the bodyside liner layer 42 may comprise wood or cotton fibers. Other possible materials are synthetic fibers, such as polyester or polypropylene fibers, or a combination of natural and synthetic fibers. Bodyside liner layer 42 is suitably utilized to help isolate the liquids held in the absorbent core 34 from the wearer's skin.

Various woven and nonwoven fabrics can be used for bodyside liner layer 42. For example, bodyside liner layer 42 may be composed of a meltblown or spunbonded web of polyolefin fibers. The bodyside liner layer 42 may also comprise a carded and/or bonded web composed of natural and/or synthetic fibers. The bodyside liner layer 42 may also be composed of a substantially hydrophobic material wherein the hydrophobic material is treated with a surfactant or otherwise processed to impart a desired level of wettability and hydrophilicity. In a particular embodiment of the present invention, the bodyside liner layer 42 may comprise a spunbonded polypropylene fabric composed of about 2.8–3.2 denier fibers formed into a web having a basis weight of about 22 grams per square meter and a density of about 0.06 grams per cubic centimeter. The fabric is treated with about 0.3 weight percent of a surfactant. The bodyside liner layer 42 may comprise a multiplicity of components, layers, or partial layers, which correspond to any of the materials disclosed herein, as well as others known in the art.

It is generally preferred that the outer cover layer 40 of the absorbent article 8 be formed from a material which is substantially impermeable to liquids. A typical outer cover layer 40 may be manufactured from a thin plastic film or other flexible liquid-impermeable material. For example, the outer cover layer 40 can be formed by a polyethylene film having a thickness of from about 0.012 millimeter to about 0.051 millimeter. When it is desirable that the outer cover layer 40 have a more clothlike feeling, it may comprise a polypropylene film laminated on one surface to a nonwoven web, such as a spunbonded web of polyolefin fibers. For example, a polypropylene film having a thickness of about 0.015 millimeter may have thermally or otherwise laminated thereto a spunbonded web of polyolefin fibers having a thickness from 1.5 to 2.5 denier per filament, which nonwoven web has a basis weight of about 24 grams per square meter. Further, the outer cover layer 40 can be formed of a woven or nonwoven fibrous web which has been totally or partially constructed or treated to impart a desired level of liquid impermeability to selected regions that are adjacent or proximate the absorbent core 34. Still further, the outer cover layer 40 may optionally be composed of a microporous material which permits vapors to escape from the absorbent core 34 and through outer cover layer 40 while preventing liquid exudates from passing through the outer cover layer 40.

The attachment elements 32 can comprise a mechanical fastener such as the hooks of a hook and loop fastening system preferably mounted on outer cover layer 40 of base structure 38. The attachment surface 33 then comprises a corresponding loop material attached to the outer cover layer 40 in front portion 10 and adapted to releasably engage with the hook material. Other well known fastening means can also be used to support the absorbent article 8 upon a person. For example, a cohesive system, an adhesive fastener system or the like may also be utilized to fasten the absorbent article 8.

Figure 3:
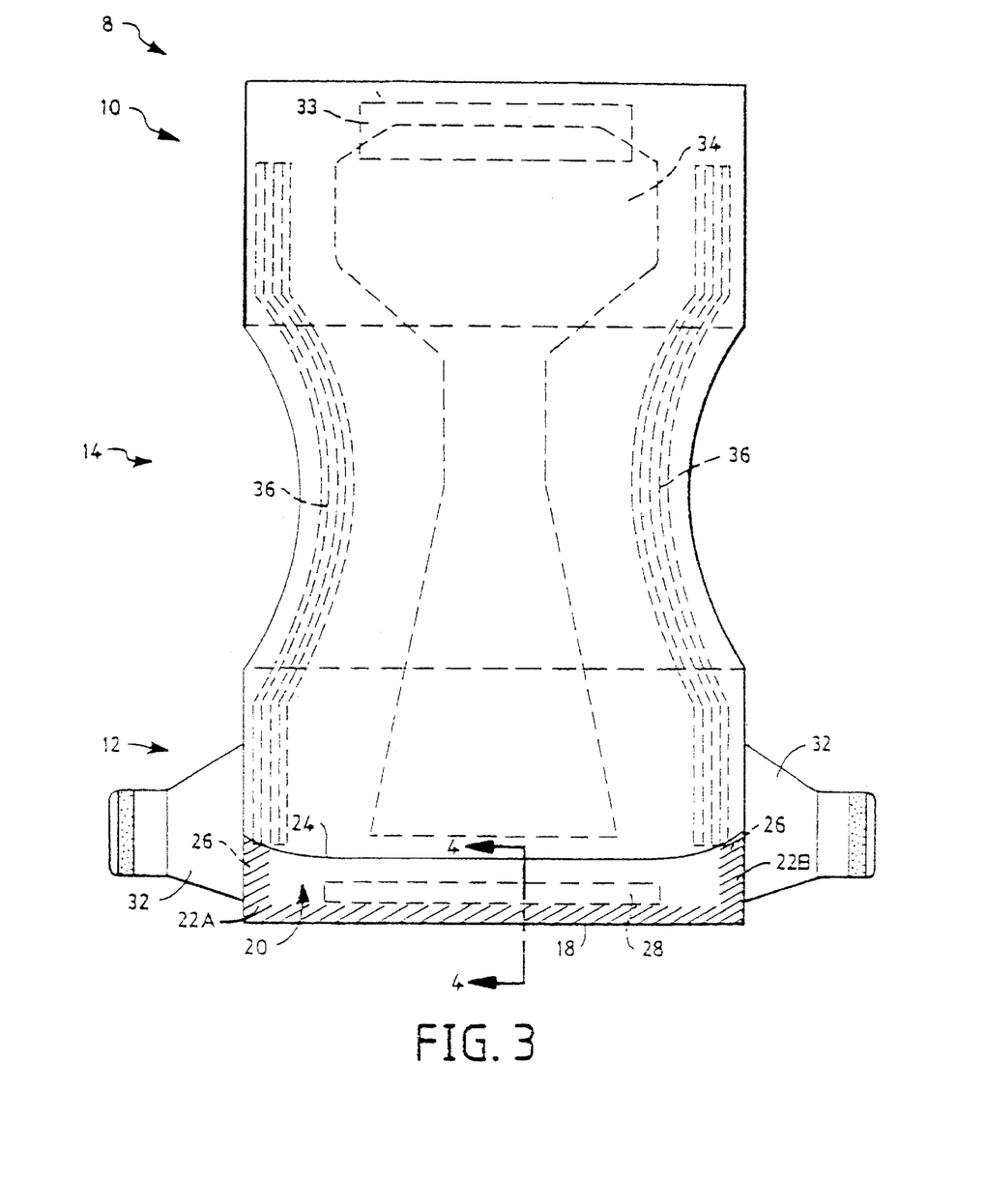
FIG. 3 illustrates a top view of a second embodiment of an absorbent article of the invention, fully extended.

Materials suitable for forming leg elastics 36 include strands, ribbons, or one or more layers of a polymeric and/or elastomeric material which may be adhered in the absorbent article 8 while the elastic is in a stretched condition. Alternatively, the elastic material can be attached, in a relaxed condition, to the absorbent article 8 while the absorbent article 8 is pleated. The leg elastics 36 may suitably comprise one or more individual strands of elastomeric material. For example, a plurality of elastic strands may be configured in a spatially separated, generally parallel arrangement as shown in FIGS. 1 and 3. The elastic strands can be distributed over the full length of at least the crotch portion 14 of the absorbent article 8 and formed of a rubber material. A suitable elastic strand may, for example, be composed of a 470 decitex LYCRA® elastomer, 620 decitex LYCRA® elastomer or other elastomers with suitable characteristics. Leg elastics 36 are preferably integrated into the base structure 38 between the outer cover layer 40 and the bodyside liner layer 42.

Rear waist elastics 44 can comprise strands, ribbons or one or more layers of a polymeric and/or elastomeric material which can be adhered to the absorbent article while elastics 44 are in a stretched condition. Rear waist elastics 44 may comprise one or more individual strands of elastomeric material, preferably in a spatially separated, generally parallel arrangement as shown in the cross-sectional view of FIG. 2. While rear waist elastics 44 can be made of similar materials to the leg elastics 36, the amount of retractive force, and generally the thickness of the respective elastic strands, or like material, is generally less.

Base structure 38 is preferably formed by adhesive or other attachment of outer cover layer 40 and bodyside liner layer 42 to each other. The absorbent core 34, waist elastics 44, leg elastics 36 and spacer 28 are all preferably located within the base structure 38 between the outer cover layer 40 and the bodyside liner layer 42. The outer cover layer 40 and bodyside liner layer 42 form base structure 38 by securement to each other such as by sewing, heat sealing, sonic bonding, adhesive bonding or the like. Similarly, the absorbent core, waist elastics, leg elastics, and spacer can be incorporated into the base structure using the same or similar technology.

While FIGS. 1 and 3 show the rear waist flap 20 attached to rear portion 12 at side edges 22A, 22B with glue 26, the use of glue 26 is not critical. Sewing, heat sealing, sonic bonding, adhesive bonding or the like can be utilized to make this attachment.

In the embodiment of FIGS. 1 and 2, rear reservoir 30 is formed in rear portion 12 of the absorbent article 8. The rear reservoir 30 is formed by the combination of rear waist flap 20, spacer 28, and rear portion 12. Rear waist flap 20 which is an integral part of the base structure 38, as an extension of the base structure 38 from rear portion 12, is attached on the side edges 22A, 22B to rear portion 12, and is folded inwardly toward the bodyside liner layer 42 on rear portion 12. Rear waist flap 20 can also be described as being formed by portions of both the outer cover layer 40 and the bodyside liner layer 42 folded inwardly toward the bodyside liner layer 42 of the rear portion 12, with the rear waist flap 20 attached at opposing side edges thereof to the rear portion 12 to thereby form the rear reservoir 30 between the rear waist flap 20 and the rear portion 12. Rear waist flap 20 and rear portion 12 of the absorbent article 8 together have a "C" configuration as shown in FIG. 2. This "C" configuration defines the general shape of the rear portion 12 as shown in FIG. 2. The rear waist elastics 44 are preferably stretched when attached across the rear waist flap 20. The rear waist elastics 44 also aid in the formation of rear reservoir 30. Spacer 28, comprising a resilient material, is generally mounted to the rear portion 12 generally parallel to the rear edge 18. The rear reservoir 30 can contain exudates such as fecal material.

Figure 4:
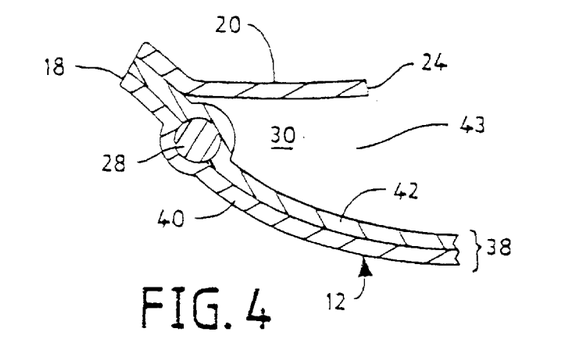
FIG. 4 illustrates a fragmentary cross-sectional view taken at 4—4 of FIG. 3.

In the embodiment of FIGS. 3 and 4, the rear waist flap 20 comprises a separate element, extending generally across the width "W" of absorbent article 8, and thus of rear portion 12. The separate element preferably has retractive elastic properties. The rear waist flap of FIG. 3 is attached to the rear portion 12 of the absorbent article 8 on side edges 22A, 22B and the rear edge 18 of the rear portion to form rear reservoir 30 sealed against exudate leakage at rear edge 18, as well as at side edges 22A, 22B. While FIG. 3 shows attachment by glue 26, the use of glue 26 is not critical. Sewing, heat sealing, sonic bonding, adhesive bonding or the like can be utilized to attach the rear waist flap 30, so long as secure attachment is achieved, along with an adequate seal against leakage.

Rear waist flap 20 can comprise an elastic member formed by a single layer of elastic material 20 as shown in FIG. 4 or multiple layers of elastic material. One exemplary preferred material for the rear waist flap 20 is a laminate of an elastomeric core layer with bicomponent nonelastic spunbonded facing layers on opposite sides of the elastomeric core layer. The elastomeric core layer preferably comprises a styrene ethylene butylene styrene terpolymer, such as a KRATON® G polymer from Shell Chemical Company. The elastomeric core layer generally provides a barrier to fluid. When placed between spunbonded facing layers, the core layer can form a 3-layer stretch-bonded laminate. While a terpolymer is preferred, other known polymers such as elastomeric copolymers can also provide an elastomeric core layer with similar properties.

As used herein, a "stretch-bonded laminate" is a multiple layer structure comprised of at least two layers in which one layer is a gatherable layer and the other layer a stretchable layer wherein stretching creates retractile forces in the layer. The layers are joined together when the stretchable layer is in a stretched condition so that, upon relaxing the layers, the gatherable layer is gathered by the retractile forces exerted by the stretchable/stretched layer. The stretchable layer can be a film of stretchable material or a plurality of strands of a stretchable material. The rear waist flap 20 is preferably stretchable only in a direction that is across the width of the absorbent article 8. Other materials, which can form the middle or elastomeric core layer of the waist flap 20, include an elastomeric material or a stretchable meltblown material, such as a meltblown layer, which is a barrier to fluid. A carded web may also comprise the elastomeric core layer. Other materials which may comprise the rear waist flap 20 of FIG. 3 include neck-bonded laminates or the like. Other conventional materials, including multiple layer structures, may be selected for rear waist flap 20 within the requirements of the stretching and sealant properties.

The rear waist flap 20 of FIGS. 3 and 4 is preferably substantially stretched when attached to the rear portion 12 of the absorbent article 8. The rear waist flap 20 then may retract to form the rear reservoir 30.

The rear waist flap 20 of FIGS. 3 and 4 can also comprise a nonelastic material. The nonelastic material preferably has rear waist elastics 44 attached thereto of the type described with respect to FIG. 1. The rear waist flap 20 can comprise materials similar to those described for the bodyside liner layer 42 and the outer cover layer 40. Further, the rear waist flap 20 can comprise a multilayer combination of materials.

Figure 6:
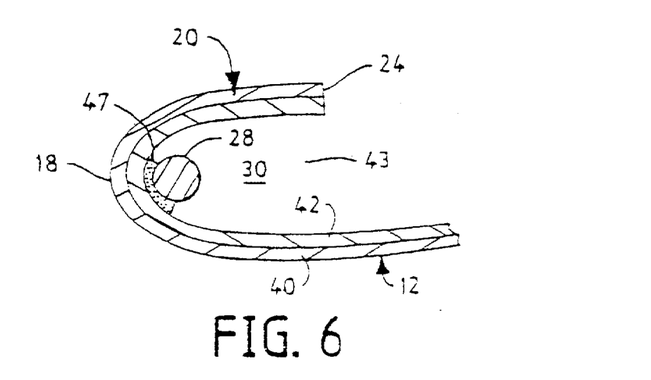
FIG. 6 illustrates a cross-sectional view as in FIG. 4, showing alternate placement of the spacer.

The spacer 28 preferably is glued or otherwise attached to the base structure 38 between outer cover layer 40 and bodyside liner layer 42 as shown in FIGS. 2 and 4. In the alternative, the spacer 28 can be otherwise attached as by glue 47, shown in FIG. 6, to base structure 38, such as to the bodyside liner layer 42 or to outer cover layer 40.

Independent of the layer or layers to which the spacer 28 is mounted, the mounting location on the layer can be selected with some discretion. For example, the spacer 28 can be mounted to the rear waist flap 20 adjacent the rear edge 18 of the absorbent article 8, to rear portion 12, or where rear portion 12 and rear waist flap 20 meet such as at rear edge 18. Thus, spacer 28 may be located in the vicinity of rear edge 18. The spacer 28 must be mounted between rear edge 18 and distal edge 24 in order to properly form rear reservoir 30.

The spacer 28 preferably has a rod-like shape. In the embodiments of FIGS. 1–4 the spacer 28 comprises an internal filler. The filler is resilient to allow some compression, curving and bending without allowing enough deformation so the rear reservoir 30 becomes too small, or collapsed. Thus, compressive deformation of spacer 28, when acted on by compressive forces encountered in normal use, is limited to amounts of deformation which maintain sufficient void volume in rear reservoir 30 to receive an effective amount of exudates from the body of the user. The resiliency of spacer 28 to bending forces ensures that the absorbent article 8 is comfortable to a user while maintaining the void volume of rear reservoir 30 and thus the ability to contain exudates and fecal material.

Figure 5:
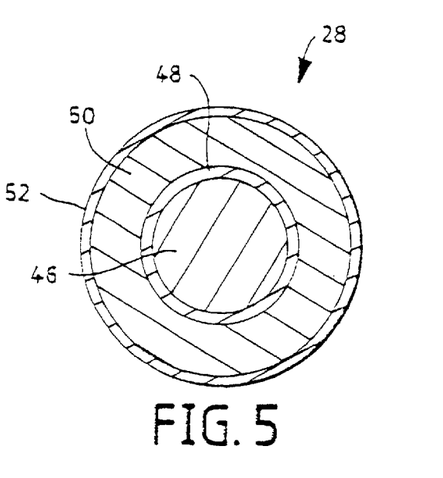
FIG. 5 illustrates a cross-sectional view of a spacer used in the invention.

FIG. 5 shows a cross-section across the thickness of one embodiment of spacer 28. In this embodiment the spacer includes the internal filler 46 of fluff formed into a rod-like shape. A first containment layer 48 of cloth, film or other containment material contains the internal filler 46 of fluff compressed therein. A second outer and cylindrical layer 50 of fluff is formed around the first containment layer 48. The second layer 50 of fluff is then enclosed within a second containment layer 52 of cloth, film, or other containment material which forms the outside of the spacer 28. The spacer 28 of FIG. 5 is, overall, a soft, flexible, resilient, compressible, rod-like component which is mounted across the rear portion 12, preferably substantially parallel to the rear edge 18 of the absorbent article 8. Thus spacer 28 can be compressed, while maintaining void volume for rear reservoir 30, and resiliently returned to substantially its original position when the compressive force is removed. With respect to spacer 28, "fluff" can comprise a regenerated cellulose fluff such as rayon. The spacer can also comprise a regenerated cellulose fluff and polyester which have been blended, or any material which is deformable, but sufficiently resilient to function as a spacer. For example, scraps of material from the cutting machines in an absorbent article assembly process may be useable as fluff.

The first and second layers 48, 52 of cloth, film or other containment materials can comprise materials similar to that taught for use as bodyside liner layer 42 or outer cover layer 40.

FIG. 7 shows a pictorial view of the absorbent article 8. In this view, the location of the rear waist flap 20 is more clearly illustrated. The rear waist flap 20, spacer 28, rear waist elastics 44 and leg elastics 36 all aid in forming rear reservoir 30 and the corresponding opening 43. While the reservoir opening 43 may temporarily be closed by forces exerted in combination with the position of the user, the combination of the spacer 28, flap 20, and elastics 44, 36 automatically reopen the flap when the user changes position, removing the closing force.

Figure 8:
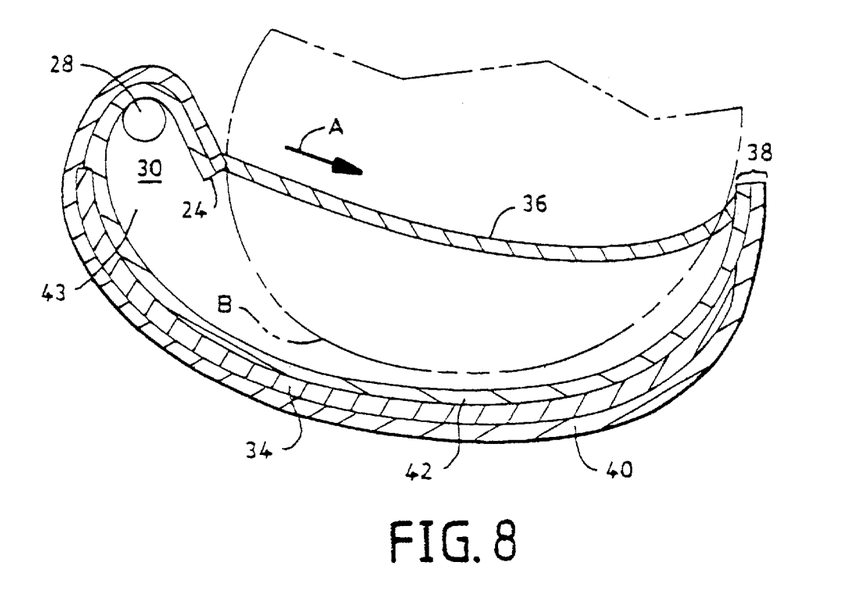
FIG. 8 illustrates a cross-sectional view taken at 8—8 of FIG. 7.

FIG. 8 taken at line 8—8 of FIG. 7 shows a cross-sectional view of the absorbent article 8. FIG. 8 illustrates the shape of the absorbent article 8 when placed upon a user's body "B". In use, leg elastics 36 pull on rear waist flap 20 in the direction of arrow "A" which urges the distal edge 24 away from the bodyside liner layer 42 and against the buttocks of the user. Thus, leg elastics 36 provide a continuous dynamic force tending to create and maintain the opening 43, across the entire width "W" of the rear waist flap 20, such that body exudates freely enter rear reservoir 30 through opening 43. In this manner, exudates do not leak or pass beyond rear edge 18 of the absorbent article 8, as can happen with conventional diapers. The leg elastics 36 extend into the rear portion 12 and provide the dynamic force which also assists in forming an inwardly-opening pocket in the rear portion 12 forward of the rear edge 18. The inwardly-opening pocket is comprised in the rear reservoir 30, typically adjacent distal edge 24.

Rear waist elastics 44 of the absorbent article provide a force tending to gather the rear waist flap 28. Gathering of the rear waist flap 28 also tends to form a pocket, in the rear portion 12, which comprises part of the rear reservoir 30.

Spacer 28 aids in creating the rear reservoir 30, by displacing the rear portion 12 from the rear waist flap 20. This displacement increases the size of the rear reservoir 30 which is then held in an open position and further expanded and sized by the rear waist elastics 44, leg elastics 36 and the rear waist flap 20.

Figure 9:
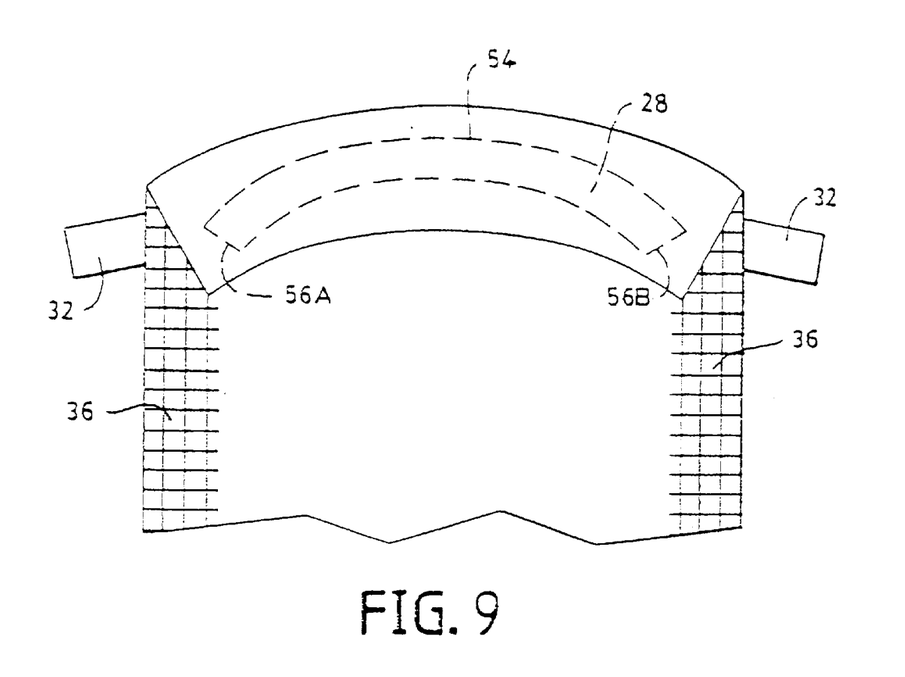
FIG. 9 illustrates a top view of the rear portion of the absorbent article of the invention.

FIG. 9 shows a partial top view of the rear portion 12 of the absorbent article 8. As shown in FIG. 9, when forming the rear reservoir 30, the spacer 28 tends to be bowed such that a midpoint 54 of the spacer 28 is displaced rearwardly of the absorbent article 8 with respect to first and second ends 56A, 56B of the spacer 28. In this manner, the spacer 28 tends to conform to the overall shape of the diaper when applied to a user's body "B". Further, bowing of the spacer 28 increases the depth of rear reservoir 30. The absorbent article 8 preferably is formed so that spacer 28 is bowed upon construction of the absorbent article 8. The absorbent article 8 may also be formed so that spacer 28 is bowed when the absorbent article 8 is applied to a user's body.

Figure 10:
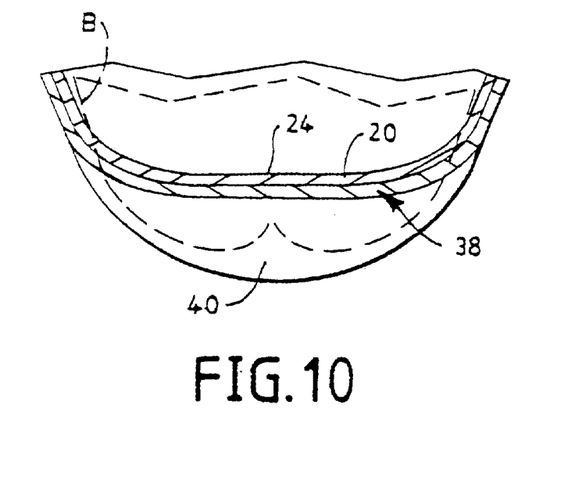
FIG. 10 illustrates a top partial cross-sectional view taken at 10—10 of FIG. 7 which shows the absorbent article applied to a user.

FIG. 10 shows a partial cross-sectional view taken at 10—10 of FIG. 7. This view shows a top view of the rear waist flap 20 against a user's body "B" and a portion of the outer cover 40 which extends outwardly from the user's body "B". The rear waist elastics 44 urge the rear waist flap 20 against the user's body "B". The leg elastics 36 shown in FIG. 8 also extend the rear waist flap 20 toward the user's body "B". This arrangement forms a tight seal between the user's waist and the rear waist flap 20.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

Having thus described the invention, what is claimed is:

1. An absorbent article having a rear portion including a rear edge, a front portion, and a crotch portion connecting said rear portion and said front portion, said absorbent article comprising:
   (a) a base structure including a first layer thereof comprising an outer cover layer and a second layer thereof comprising a bodyside liner layer
   (b) an absorbent member between said outer cover layer and said bodyside liner layer;
   (c) a rear waist flap extending from the vicinity of said rear edge of said rear portion toward said crotch portion to thereby define a rear reservoir between said rear waist flap and said rear portion; and
   (d) a spacer mounted to at least one of said rear portion and said rear waist flap, effectively occupying space in said rear reservoir, thereby spacing said rear waist flap from said rear portion, compressive deformation of said spacer by the body of a user being limited to amounts of deformation which maintain sufficient void volume in said rear reservoir to receive an effective amount of exudate from the body of the user.

2. An absorbent article according to claim 1 wherein said spacer is located between said outer cover layer and said bodyside liner layer.

3. An absorbent article according to claim 1 wherein said spacer comprises a regenerated cellulose fluff.

4. An absorbent article according to claim 1 wherein said spacer comprises fluff contained within a rod-like shaped structure, said fluff and said rod-like shaped structure, in combination, maintaining the sufficient void volume in said rear reservoir during normal use conditions.

5. An absorbent article according to claim 1, the limit on compressive deformation of said spacer by the body of the user preventing collapse of said rear reservoir.

6. An absorbent article according to claim 1 wherein said rear waist flap extends from said rear edge outwardly around said spacer and toward said crotch portion.

7. An absorbent article according to claim 6 wherein said rear waist flap comprises portions of both said outer cover layer and said bodyside liner layer folded inwardly toward said bodyside liner layer of said rear portion, said rear waist flap being attached, at opposing side edges of said absorbent, article to said rear portion to thereby form said rear reservoir between said rear waist flap and said rear portion.

8. An absorbent article according to claim 7 wherein said rear waist flap, in combination with at least part of said rear portion of said absorbent article, extends in a "C" configuration in defining said rear reservoir.

9. An absorbent article according to claim 6 wherein rear waist elastics are attached across said rear waist flap, said rear waist elastics, in combination with at least said spacer, said rear portion, and said rear waist flap, forming said rear reservoir.

10. An absorbent article according to claim 6 wherein said rear waist flap comprises an elastic member attached to said rear portion at said rear edge and at opposing side edges of said absorbent article.

11. An absorbent article according to claim 10 wherein said elastic member is substantially stretched when attached to said rear portion, said elastic member, when released from a stretched condition, retracting said rear portion to form in part said rear reservoir.

12. An absorbent article according to claim 6, including an opening for receiving exudates into said rear reservoir, said opening having a length extending across a width of said absorbent article generally corresponding to a respective width of said rear reservoir.

13. An absorbent article according to claim 1 wherein said rear waist flap comprises a nonelastic material extending from said rear portion at said rear edge and at opposing side edges, said nonelastic material having waist elastics attached thereto.

14. An absorbent article according to claim 1, including an opening for receiving exudates into said rear reservoir, said opening having a length extending across a width of said absorbent article corresponding to a respective width of said rear reservoir.

15. An absorbent article according to claim 1, said spacer being located in the vicinity of said rear edge, having first and second ends, and a midpoint, and being bowed such that the midpoint of said spacer is displaced rearwardly in said absorbent article with respect to said first and second ends.

16. An absorbent article as in claim 1, including an opening in said rear reservoir, disposed toward said crotch portion, for entrance of exudates, through the opening, into said rear reservoir.

17. An absorbent article having a rear portion including a rear edge, a front portion, and a crotch portion connecting said rear portion and said front portion, said absorbent article comprising:
   (a) a base structure including a first layer thereof comprising an outer cover layer and a second layer thereof comprising a bodyside liner layers, extending over said front portion, said rear portion, and said crotch portion;
   (b) an absorbent member between said outer cover layer and said bodyside liner layer,
   (c) a rear waist flap extending from the vicinity of said rear edge of said rear portion toward said crotch portion to thereby define a rear reservoir between said rear waist flap and said rear portion; and,
   (d) a spacer mounted to at least one of said rear portion and said rear waist flap, said spacer extending across said rear portion, and effectively occupying space in said rear reservoir, and thereby spacing said rear waist flap from said rear portion to effectively maintain sufficient void volume in said rear reservoir to receive an effective amount of exudates from the body of the user.

18. An absorbent article according to claim 17 wherein said spacer is located between said outer cover layer and said bodyside liner layer.

19. An absorbent article according to claim 17 wherein said spacer comprises regenerated cellulose fluff.

20. An absorbent article according to claim 17 wherein said spacer comprises fluff contained within a rod-like shaped structure, said fluff and said rod-like shaped structure, in combination, spacing said rear waist flap and said rear portion from each other.

21. An absorbent article according to claim 17 wherein said rear waist flap comprises both said outer cover layer and said bodyside liner layer folded inwardly toward said bodyside liner layer on said rear portion, with said rear waist flap attached at opposing side edges of said absorbent article to said rear portion to thereby form said rear reservoir between said rear waist flap and said rear portion.

22. An absorbent article according to claim 21 wherein said rear waist flap, in combination with at least part of said rear portion of said absorbent article, extends in a "C" configuration in defining said rear reservoir.

23. An absorbent article according to claim 17 wherein rear waist elastics are attached across said rear waist flap, said rear waist elastics, in combination with at least said spacer, said rear portion, and said rear waist flap, forming said rear reservoir.

24. An absorbent article according to claim 17 wherein said rear waist flap comprises an elastic member attached to said rear portion at said rear edge and at opposing side edges of said rear portion.

25. An absorbent article according to claim 24 wherein said elastic member is substantially stretched when attached to said rear portion.

26. An absorbent article according to claim 17 wherein said rear waist flap comprises a nonelastic material extending from said rear portion at said rear edge and opposing side edges, said nonelastic material having waist elastics attached thereto.

27. An absorbent article according to claim 17, including an opening for receiving exudates into said rear reservoir, said opening having a length extending across a width of said absorbent article corresponding to a respective width of said rear reservoir.

28. An absorbent article according to claim 17, said spacer being located in the vicinity of said rear edge, having first and second ends, and a midpoint, and being bowed such that the midpoint of said spacer is displaced rearwardly in said absorbent article with respect to said first and second ends.

29. An absorbent article according to claim 17, including first and second leg elastics at respective opposing first and second side edges of said absorbent article in said crotch portion, said first and second leg elastics extending into said rear portion and assisting in forming an inwardly-opening pocket in said rear portion, forward of said rear edge.

30. An absorbent article according to claim 17, compressive deformation of said spacer by the body of a user being limited to amounts of deformation which maintain sufficient void volume in said rear reservoir to receive an effective amount of exudates from the body of the user.

31. An absorbent article as in claim 17, including an opening in said rear reservoir, disposed toward said crotch portion, for entrance of exudates, through the opening, into said rear reservoir.

32. An absorbent article having a front edge, a rear edge, and opposing first and second side edges, and including a rear portion including a rear edge and a distal edge, a front portion, and a crotch portion connecting said rear portion and said front portion, said absorbent article comprising:

(a) a base structure including a first layer thereof comprising an outer cover layer and a second layer thereof comprising a bodyside liner layer;

(b) an absorbent member between said outer cover layer and said bodyside liner layer;

(c) a rear waist flap extending from the vicinity of said rear edge of said rear portion toward said crotch portion to thereby define a rear reservoir; and (d) a spacer disposed at at least one of said rear portion and said rear waist flap, and spacing said rear waist flap from said rear portion, said spacer having a thickness, said rear waist flap being spaced from said rear portion by the thickness of said spacer.

33. An absorbent article according to claim 32, said rear waist flap being attached, at opposing first and second side edges thereof to said base structure.

34. An absorbent article according to claim 32, said spacer extending across a width of said absorbent article.

35. An absorbent article according to claim 34 wherein said spacer is located between said outer cover layer and said bodyside liner layer.

36. An absorbent article according to claim 34 wherein said spacer comprises a regenerated cellulose fluff.

37. An absorbent article according to claim 34 wherein said spacer comprises fluff contained within a rod-like shaped structure, said fluff and said rod-like shaped structure, in combination, being sufficiently resistant to compressive deformation by the body of the user to space said rear waist flap and said rear portion from each other when said spacer is so compressed.

38. An absorbent article according to claim 34 wherein rear waist elastics are attached across said rear waist flap, said rear waist elastics, in combination with said spacer, said rear portion, and said rear waist flap, forming said rear reservoir.

39. An absorbent article according to claim 34 said spacer being located in the vicinity of said rear edge, having first and second ends, and a midpoint, and being bowed such that the midpoint of said spacer is displaced rearwardly in said absorbent article with respect to said first and second ends.

40. An absorbent article according to claim 32 wherein said rear waist flap comprises both said outer cover layer and said bodyside liner layer.

41. An absorbent article according to claim 40 wherein said rear waist flap, in combination with at least part of said rear portion of said absorbent article, extends in a "C" configuration in defining said rear reservoir.

42. An absorbent article according to claim 32, including an opening for receiving exudates into said rear reservoir, said opening having a length extending across a width of said absorbent article corresponding to a respective width of said rear reservoir.

43. An absorbent article according to claim 32, including an opening for receiving exudates into said rear reservoir, said opening having a length extending across a width of said absorbent article corresponding to a respective width of said rear reservoir, said rear waist flap comprising portions of both said outer cover layer and said bodyside liner layer folded inwardly toward said bodyside liner layer of said rear portion, with said rear waist flap attached at opposing side edges thereof to said rear portion to thereby form said rear reservoir between said rear waist flap and said rear portion.

44. An absorbent article according to claim 32, including first and second leg elastics at respective opposing first and second side edges of said absorbent article in said crotch portion, said first and second leg elastics extending into said rear portion and assisting in forming an inwardly-opening pocket in said rear portion, forward of said rear edge.

45. An absorbent article as in claim 32, including an opening in said rear reservoir, disposed toward said crotch portion, for entrance of exudates, through the opening, into said rear reservoir.

* * * * *